(12) United States Patent
Taylor et al.

(10) Patent No.: US 9,297,569 B2
(45) Date of Patent: Mar. 29, 2016

(54) SYSTEM AND METHOD FOR PROVIDING EFFICIENT COOLING WITHIN A TEST ENVIRONMENT

(75) Inventors: Mark A. Taylor, McKinney, TX (US); Don R. Tolbert, McKinney, TX (US)

(73) Assignee: Raytheon Company, Waltham, MA (US)

( * ) Notice: Subject to any disclaimer, the term of this patent is extended or adjusted under 35 U.S.C. 154(b) by 277 days.

(21) Appl. No.: 13/190,999

(22) Filed: Jul. 26, 2011

(65) Prior Publication Data
US 2012/0023979 A1    Feb. 2, 2012

Related U.S. Application Data

(60) Provisional application No. 61/368,219, filed on Jul. 27, 2010.

(51) Int. Cl.
F25B 7/00    (2006.01)
F25D 13/00   (2006.01)
G01N 17/00   (2006.01)

(52) U.S. Cl.
CPC ............ *F25D 13/00* (2013.01); *G01N 17/002* (2013.01)

(58) Field of Classification Search
CPC .... F25B 2400/24; F25B 7/00; F25B 2400/06; F25B 2400/075
USPC ...................... 62/79, 335, 333, 175
See application file for complete search history.

(56) References Cited

U.S. PATENT DOCUMENTS

| 4,272,966 A | 6/1981 | Niemann et al. |
|---|---|---|
| 4,300,623 A | 11/1981 | Meckler |
| 4,550,574 A * | 11/1985 | Hohman ................... 62/197 |
| 6,305,180 B1 * | 10/2001 | Miller et al. ............ 62/259.2 |
| 6,694,750 B1 | 2/2004 | Lifson et al. |
| 6,829,903 B2 * | 12/2004 | Lee et al. .................. 62/229 |
| 6,842,718 B2 | 1/2005 | Byrd et al. |
| 7,856,831 B2 | 12/2010 | Flinner et al. |
| 2002/0092318 A1 * | 7/2002 | Tipton et al. ............... 62/510 |
| 2002/0148239 A1 * | 10/2002 | Trieskey ..................... 62/79 |
| 2006/0196199 A1 * | 9/2006 | Hunt ........................ 62/132 |
| 2006/0201188 A1 * | 9/2006 | Kopko ....................... 62/333 |
| 2007/0107449 A1 * | 5/2007 | Crane et al. ................ 62/175 |
| 2008/0104982 A1 * | 5/2008 | Sunderland ............. 62/228.1 |

* cited by examiner

*Primary Examiner* — Jonathan Bradford
*Assistant Examiner* — Elizabeth Martin

(57) ABSTRACT

A system and method for cooling an environmental test chamber is described where a controller is in communication with an auxiliary cooling unit and the primary refrigeration unit. A first chamber temperature measurement associated with the environmental test chamber is received, and the heat load associated with a target temperature is determined. Based on the first chamber temperature measurement and the heat load, it is determined that the auxiliary cooling unit can sustain the target temperature. In response to the determination, the controller is used to transmit a signal to power on the auxiliary cooling unit and a signal to time out the primary refrigeration unit.

20 Claims, 3 Drawing Sheets

SYSTEM AND METHOD FOR PROVIDING EFFICIENT COOLING WITHIN A TEST ENVIRONMENT

RELATED APPLICATION

This application claims benefit under 35 U.S.C. §119(e) of U.S. Provisional Application Ser. No. 61/368,219, entitled "Efficient Cooling System," filed Jul. 27, 2010, by Mark A. Taylor et al., which is incorporated herein by reference.

TECHNICAL FIELD OF THE DISCLOSURE

This disclosure generally relates to cooling systems and methods, and more particularly, to an system and method for providing efficient cooling within a test environment.

BACKGROUND

Products under development are often tested to ensure they will operate properly under a variety of operating conditions. In many cases, products may be tested in environmental chambers that may simulate various types of operating conditions. For example, products may be tested at extreme temperature conditions, at differing humidity levels, and/or under exposure to various chemicals that may adversely affect their proper operation.

Because the products may be tested for long durations of time or under a variety of conditions, the environmental chambers used to test these products may require large amounts of energy. As energy costs have risen, the cost of testing such products have also risen. In addition, public concern about the impact that energy usage may have on global climate change has focused more interest on reducing overall energy usage.

SUMMARY

In accordance with the present disclosure, disadvantages and problems associated with previous and existing cooling systems may be reduced or eliminated.

In certain embodiments, a method for cooling includes providing a controller in communication with an auxiliary cooling unit and a primary refrigeration unit. A first chamber temperature measurement associated with an environmental test chamber is received, and the heat load associated with a target temperature is determined. Based on the first chamber temperature measurement and the heat load, it is determined that the auxiliary cooling unit can sustain the target temperature. In response to the determination, the controller is used to transmit a signal to power on the auxiliary cooling unit and a signal to time out the primary refrigeration unit.

Certain embodiments of the disclosure may provide one or more technical advantages. For example, certain embodiments of the cooling system may provide enhanced efficiency over cooling systems that do not have an auxiliary refrigeration apparatus. As a particular example, a primary refrigeration apparatus having a relatively large cooling capacity may be used in certain situations for the rapid cooling of the environmental test chamber or for simulating thermal shock conditions in which the temperature is modified in a relatively fast manner. In other situations, however, where only a portion of the available cooling capacity of the primary refrigeration apparatus is required to cool the environmental test chamber, an auxiliary cooling unit that has less cooling capacity than the primary refrigeration unit may be used As a result, a technical advantage may be that the cooling system results in more efficient use of energy during operation of the environmental test chamber.

In certain embodiments, the cooling system of the present disclosure may provide an auxiliary refrigeration apparatus that may be operated in lieu of primary refrigeration apparatus to cool the inner cavity of the chamber in situations in which the cooling capacity of primary refrigeration apparatus is significantly higher than the needs of the chamber. For example, though a primary refrigeration unit may be used to obtain a target temperature, the auxiliary cooling unit may be used thereafter to maintain the target temperature. Another technical advantage may be that the auxiliary cooling unit may be capable of maintaining the temperature of the environmental test chamber at a target temperature that is below −20 degrees Celsius.

In other embodiments, another technical advantage may be that the auxiliary cooling unit may be operated in conjunction with the primary refrigeration unit to result in a more rapid cooling of the environmental test chamber. As a result, the target temperatures required for flash cooling may be more quickly obtained by the simultaneous operation of both the primary refrigeration unit and the auxiliary cooling unit.

In certain embodiments, the auxiliary cooling unit may include a dual stage refrigeration unit having a cascade configuration of compressors and heat exchangers. In particular embodiments, the operation of the auxiliary cooling unit may be transitioned from dual stage operation to single stage operation when the target temperature is or nearly is obtained.

Certain embodiments of the present disclosure may provide some, all, or none of these advantages. Certain embodiments may provide one or more other technical advantages, one or more of which may be readily apparent to those skilled in the art from the figures, descriptions, and claims included herein.

BRIEF DESCRIPTION OF THE DRAWINGS

To provide a more complete understanding of embodiments of the present disclosure and the features and advantages thereof, reference is made to the following description taken in conjunction with the accompanying drawings, in which.

DESCRIPTION OF EXAMPLE EMBODIMENTS

An environmental test chamber typically includes a refrigeration system that is configured to achieve desired testing conditions within a required time period. Often the refrigeration system may be configured to achieve a target temperature in a relatively short period of time. For example, rapid cooling may be appropriate where only a short amount of time is available for deriving useful test results. As another example, rapid cooling may be appropriate where thermal shock conditions are simulated by alternatively heating and/or cooling the product in a rapid manner. Conventional refrigeration systems providing rapid cooling, however, typically have high cooling capacities that may draw relatively large amounts of electrical power during their operation. As a result, conventional environmental test chambers are often not very energy efficient during other situations, such as when long term tests are conducted in which products are to be maintained at specified temperatures over an extended period of time.

Figure 1:
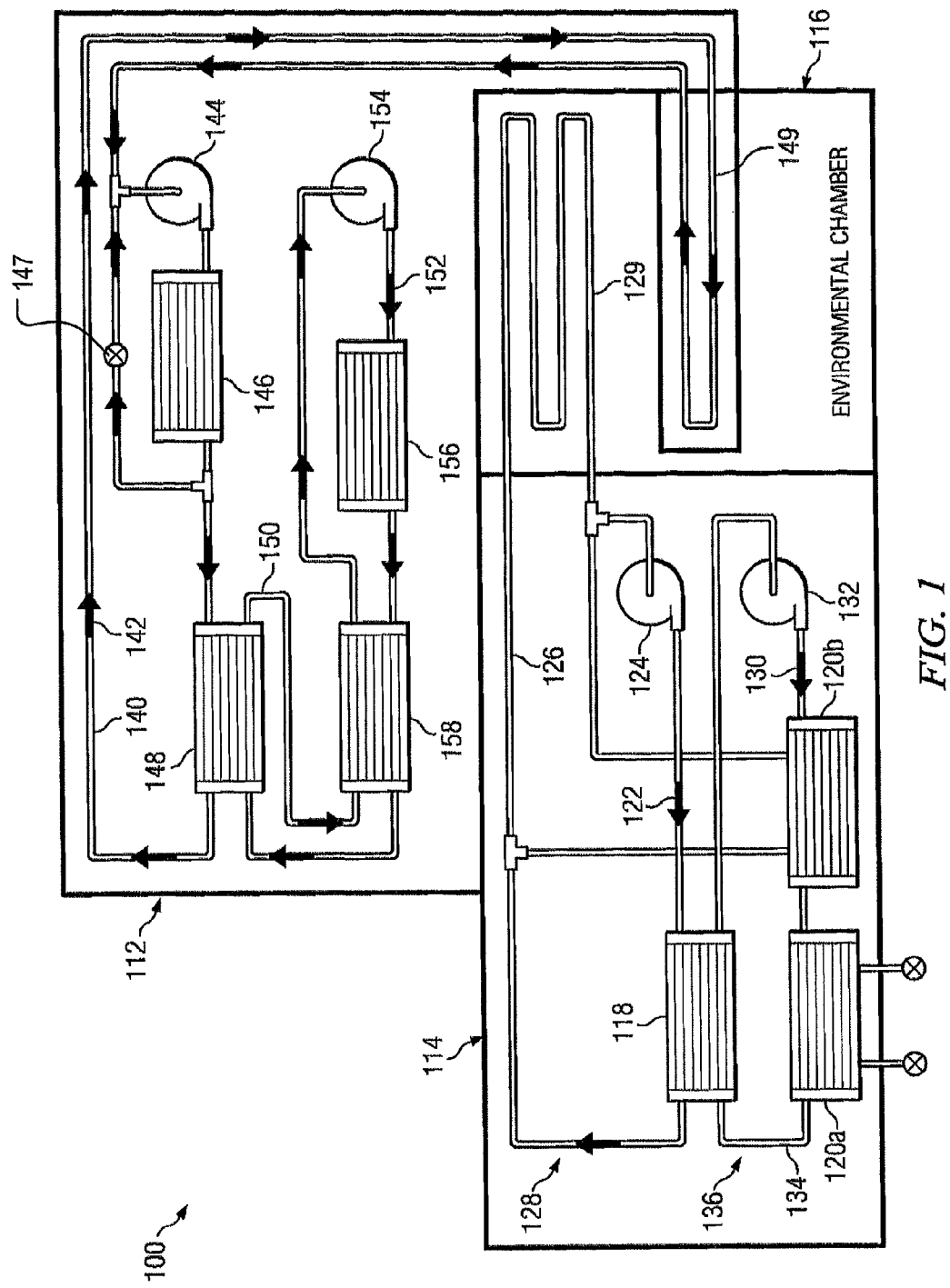
FIG. 1 illustrates an exemplary cooling system, according to certain embodiments of the present disclosure.

FIG. 1 illustrates an exemplary cooling system 100 according to certain embodiments of the present disclosure. As depicted, cooling system 100 includes both an auxiliary cooling unit 112 and a primary refrigeration unit 114 for cooling within cooling chamber 116. Each of the auxiliary cooling unit 112 and primary refrigeration unit 114 may be selectively operated based on the load required to obtain a target temperature within cooling chamber 116. For example, in particular embodiments, primary refrigeration unit 114 may be selectively operated and used to reduce the temperature within cooling chamber 116 to a target temperature or to within a target range of temperatures. After a desired temperature is obtained, primary refrigeration unit 114 may be powered down, and auxiliary cooling unit 112 may then be powered up. The more efficient auxiliary cooling unit 112 may then be used to maintain the temperature within cooling chamber 116 at the target temperature or within the target range of temperatures.

As depicted, primary refrigeration unit 114 is a cascade or "dual stage" refrigeration system that includes multiple heat exchangers and compressors arranged in a cascade configuration. Specifically, primary refrigeration unit 114 includes a primary heat exchanger 118 and at least one secondary heat exchanger 120a and 120b. Although two secondary heat exchangers 120a and 120b are depicted, it is recognized that primary refrigeration unit 114 is merely one example configuration of a refrigeration unit. Primary refrigeration unit 114 may include fewer or more components in other embodiments.

Primary heat exchanger 118 comprises a condenser coil and operates to receive first refrigerant 122 from primary compressor 124 via a fluid line 126. In addition to coupling primary heat exchanger 118 and primary compressor 124, fluid line 126 forms a first closed loop 128 for the circulation of first refrigerant 122 within primary refrigeration unit 114. As depicted, fluid line 126 includes a chamber portion 129 disposed within environmental chamber 116. As first refrigerant 122 travels through chamber portion 129 of fluid line 126, refrigerant 122 operates to cool environmental chamber 116 to a desired temperature or range of temperatures.

In contrast to primary heat exchanger 118, secondary heat exchangers 120a and 120b include condenser coils. Secondary heat exchangers 120a and 120b receive a second refrigerant 130 from secondary compressor 132 via fluid line 134. Fluid line 134 forms a second closed loop 136 for the circulation of second refrigerant 130 within primary refrigeration unit 114. As depicted, fluid line 134 is configured to circulate second refrigerant 130 through primary heat exchanger 118. As a result, primary heat exchanger 118 may operate to transfer heat from first refrigerant 122 to second refrigerant 130 and, thus, reduce the temperature of first refrigerant 122.

In this manner, secondary compressor 132 and secondary heat exchangers 120a and 120b operate to cool the condenser coil of primary heat exchanger 118 such that the temperature of first refrigerant 122 may be reduced and a relatively lower temperature of environmental chamber 116 may be achieved. The use of the secondary compressor 132 and second refrigerant 122 to cool first closed loop 128 allows the use of a refrigerant with a lower boiling point in first closed loop 128 so that first closed loop 128 can cool to lower temperatures. Thus, the cascade configuration is able to cool to lower temperatures than a non-cascade configuration.

It is generally recognized that the size of primary and secondary compressors 124 and 132 may vary and may be selected based on the maximum cooling rate required and the size of environmental chamber 116. In one particular embodiment, however, primary and secondary compressors 124 and 132 may include commercially available 30 hp compressors. Such compressors may be sufficient for cooling an environmental chamber of approximately 125 cubic feet from 70 degrees Celsius to a temperature of approximately −55 degrees Celsius in approximately 15 minutes. It is generally recognized, however, that provided sizes and dimensions are for example purposes only, and compressors 124 and 132 may be sized as appropriate for cooling the space of environmental chamber 116. Furthermore, while primary refrigeration unit 114 is described and depicted as including a cascade or dual refrigeration system, primary refrigeration unit 114 may alternatively include a single stage unit circulating a single closed loop of refrigerant.

While primary refrigeration unit 114 may be sufficient alone to cool the temperature within environmental chamber 116 to a temperature of approximately −20 degrees Celsius or higher, certain test conditions may require the temperature of environmental chamber 116 to be further reduced. Accordingly, cooling system 100 includes an auxiliary cooling unit 112 that may be selectively operated to result in the cooling of environmental chamber 116 to temperatures below −20 degrees Celsius. In certain embodiments, and as described in more detail below, auxiliary cooling unit 112 may be selectively operated in cooperation with primary refrigeration unit 114 to result in temperatures between −20 degrees Celsius and −65 degrees Celsius.

As depicted, auxiliary cooling unit 112 includes multiple heat exchangers and compressors arranged in a cascade configuration for circulating two closed loops of refrigerant. As illustrated, a first fluid line 140 circulates a first refrigerant 142 between a primary compressor 144, a heat exchanger 146, and a cascade heat exchanger 148 in a first closed loop.

More specifically, primary compressor 144 may receive first refrigerant 142 and compress first refrigerant 142 into a gas state. First refrigerant 142 is then transported via first fluid line 140 to heat exchanger 146, which includes a water cooled condensor coil for decreasing the temperature of first refrigerant 142. In particular embodiments, first refrigerant 142 has a boiling point or condensing point such that heat exchanger 146 may operate to cool first refrigerant 142 without condensing first refrigerant 142. First refrigerant 142 may then be directed from heat exchanger 146 to cascade heat exchanger 148, which operates to further decrease the temperature of first refrigerant 142 and condense first refrigerant 146 back into a liquid. An auxiliary chamber portion 149 of fluid line 148 then transports first refrigerant 142 through environmental chamber 116 before being returned to primary compressor 144. As first refrigerant 142 travels through auxiliary chamber portion 149 of fluid line 148, first refrigerant 142 changes to a gas and operates to reduce the temperature of environmental chamber 116.

In particular embodiments, a portion of first refrigerant 142 may be removed from first fluid line 140 as first refrigerant 142 is exiting heat exchanger 146. A solenoid valve 147 may be used to selectively control the amount of first refrigerant 142 that is actually being transported to auxiliary chamber portion 149 of fluid line 148. Stated differently, solenoid valve 147 may be selectively opened and closed to control the amount of first refrigerant 142 that is transported to environmental chamber 116.

As depicted, auxiliary cooling unit 112 also includes a second fluid line 150 that circulates a second refrigerant 152 between a secondary compressor 154, a condensor 156, a sub-cooler 148, and cascade heat exchanger 148 in a second closed loop. More specifically, secondary compressor 154 may receive second refrigerant 152 and compress second refrigerant 152 as a gas state. Second refrigerant 152 is then transported via second fluid line 150 to condensor 156, which includes a water cooled condensor coil for decreasing the temperature of second refrigerant 152 and condensing second refrigerant 152 into a liquid. Second refrigerant 152 may then be directed from condensor 156 to sub-cooler 158, which may include a heat exchanger for further decreasing the temperature of second refrigerant 152.

Second fluid line 150 may then transport second refrigerant 152 to cascade heat exchanger 148. As described above, cascade heat exchanger 148 operates to decrease the temperature of first refrigerant 142 and condense first refrigerant 146 back into a liquid. Thus, heat may be transferred from first refrigerant 146 to second refrigerant 152. Second refrigerant 152 may exit cascade heat exchanger 148 in a gaseous state and be transported back to sub-cooler 158. The cold gas received from the cascade heat exchanger 148 operates to cool the liquid refrigerant also passing through sub-cooler 148. The second refrigerant 152 is then returned to secondary compressor 154. In this manner, the circulation of second refrigerant 152 may be used to reduce the temperature of first refrigerant 142 and a relatively lower temperature of environmental chamber 116 may be achieved.

In certain embodiments, auxiliary cooling unit 112 has a relatively lower cooling capacity than the cooling capacity of primary refrigeration unit 114. Because auxiliary cooling unit 112 is selectively operated as an auxiliary unit, the relative size of the compressors 144 and 154 may be smaller than those of the compressors 124 and 132 of primary refrigeration unit 114. For example, in one particular embodiment, primary and secondary auxiliary compressors 144 and 154 may include commercially available 6 hp compressors. When used in conjunction with primary refrigeration unit 114, such compressors may be sufficient for further decreasing the temperature within environmental chamber 116 to a temperature that is less than 25 degrees Celsius. For example, in certain embodiments, primary refrigeration unit 114 and auxiliary cooling unit 112 may be simultaneously operated to reduce the temperature within environmental chamber 116 to a temperature of approximately −65 degrees Celsius.

Additionally, because auxiliary cooling unit 112 may operate at a relatively lower energy usage level than primary refrigeration unit 114, auxiliary cooling unit 112 may be used to improve the efficiency of primary refrigeration unit 114 under certain operating conditions. In certain embodiments, operation of the smaller auxiliary compressors 144 and 154 of auxiliary cooling unit 112 in lieu of the larger compressors 124 and 132 of primary refrigeration unit 114 may reduce energy consumption by the system 100 by as much as 90 percent. Although actual energy savings may depend on the specific temperature requirements and cycles, it is recognized that system 100, which incorporates auxiliary cooling unit 112, may reduce energy consumption by an amount between approximately 50 and 90 percent.

For example, in certain situations, primary refrigeration unit 114 must be operated at full capacity to achieve the desired test conditions. Specifically, where rapid cooling of environmental chamber 116 is desired or where thermal shock conditions are being simulated, primary refrigeration unit 114 may be operated at full capacity. Auxiliary cooling unit 112 may be simultaneously operated with primary refrigeration unit 114 to reduce the amount of time required to obtained the desired test conditions. The additional cooling capacity of auxiliary cooling unit 112 may result in the temperature being reduced at a faster rate than where primary refrigeration unit 114 is used alone. As a result the overall efficiency of the system may be improved.

In other situations, only a portion of the available cooling capacity of primary refrigeration unit 114 may be required to maintain testing conditions. For example, in certain testing conditions, primary refrigeration unit 114 may be used (either alone or in conjunction with auxiliary cooling unit 112) to obtain the desired test environment. However, because less cooling capacity may be required to maintain environmental chamber 116 at the desired temperature than was required to obtain the desired temperature, operation of primary refrigeration unit 114 may result in a relatively inefficient use of energy while maintaining testing conditions. Accordingly, in certain embodiments, operation of primary refrigeration unit 114 may be stopped after a target temperature or range of temperatures is obtained. Auxiliary cooling unit 112 may then be used to maintain the temperature of environmental chamber 116 within the desired testing conditions. In this manner, auxiliary cooling unit 112 may be operated in lieu of primary refrigeration unit 114 to maintain the desired temperature of environmental chamber 116. As a result, the overall efficiency of the system may be improved.

In certain embodiments, auxiliary cooling unit 112 may be configured as a retrofit device for an existing, commercially available primary refrigeration unit 114 with an environmental test chamber 116. That is, auxiliary cooling unit 112 may be configured on a commercial off-the-shelf (COTS) primary refrigeration unit to enhance the operating efficiency of the COTS environmental test chamber in certain embodiments.

Figure 2:
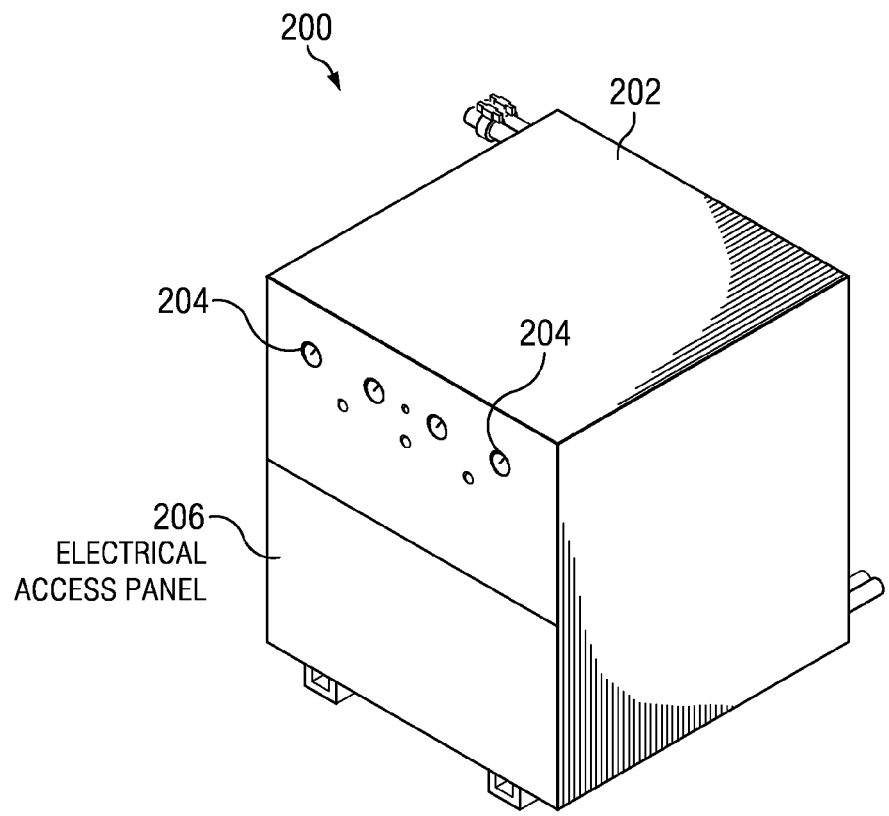
FIG. 2 illustrates an exterior view of an exemplary embodiment of an auxiliary cooling unit, according to certain embodiments of the present disclosure.

FIG. 2 illustrates an exterior view of an exemplary embodiment of the auxiliary cooling unit 200. Auxiliary cooling unit 200 may include components similar to those described above with regard to auxiliary cooling unit 112 of FIG. 1. As depicted, auxiliary cooling unit 200 includes a housing 202 for enclosing some or all of the elements of auxiliary cooling unit 200. Additionally, auxiliary cooling unit 200 includes meters 204 and a removable access panel 206 that may be used to control the operation of auxiliary cooling unit 200 and/or primary refrigeration unit 114. Removable access panel 206 may allow access to the components housed within housing 202 such that they may be serviced in a relatively easy manner. Meters 204 may provide information relating to the operation of auxiliary cooling unit 200, such as, for example, pressure, horsepower, temperature, or other measurable parameters.

It is generally recognized that housing 202 may be any size that is suitable for containing the various elements of auxiliary cooling unit 200. The size of housing 202 may depend upon the size of compressors within auxiliary cooling unit 200. For example, in one particular embodiment where auxiliary cooling unit 200 includes 6 hp compressors, housing 202 may be approximately 36 inches×36 inches×36 inches in size. Thus, housing 202 may be much smaller than the housing of a primary refrigeration unit that may include two 25 to 30 horsepower (HP) compressor units.

Figure 3:
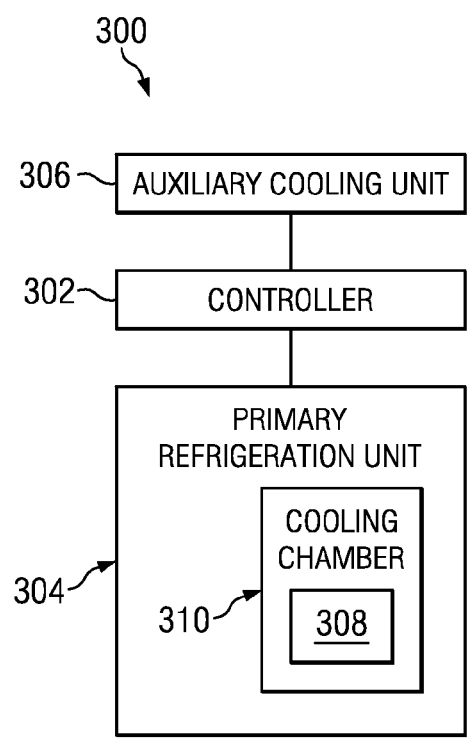
FIG. 3 illustrates an exemplary cooling system having a controller for selectively controlling the operation of the primary and auxiliary cooling units, according to certain embodiments of the present disclosure.

FIG. 3 illustrates an exemplary cooling system 300 that includes a controller 302 for selectively controlling the operation of the primary and auxiliary cooling units. Primary refrigeration unit 304 and auxiliary cooling unit 306 may be configured and operate similarly to primary refrigeration unit 114 and auxiliary cooling unit 112 described above with regard to FIG. 1. It is generally recognized that, where primary refrigeration unit 114 comprises a commercially available off-the shelf refrigeration unit, such a unit typically includes a controller for controlling the operation of that unit. However, where an auxiliary cooling unit 306 is incorporated into system 300, an additional controller 302 may be incorporated into the system for selectively operating both the primary refrigeration unit 304 and the auxiliary cooling unit 306 based on the required temperature conditions. Controller 302 may override or replace any existing controller associated with primary refrigeration unit 304.

Controller 302 may include digital logic and/or analog circuitry for controlling operation of cooling system 300. In certain embodiments, controller 302 may include a processor that executes instructions stored in a memory. In operation, controller 302 may control primary refrigeration unit 304 and auxiliary cooling unit 306 to cool the cooling chamber 308 with a relatively high degree of efficiency. For example, controller 302 may cause primary refrigeration unit 304 to operate during occasions of peak load but cause primary refrigeration unit 304 to be shut down and auxiliary cooling unit 306 to be operated at lower loads.

In certain embodiments, controller 302 may operate primary refrigeration unit 304 and auxiliary cooling unit 306 based on temperature feedback information. Specifically, a thermometer or other temperature measurement device or sensor 308 may be placed within environmental cooling chamber 308. Temperature sensor 308 may measure the temperature of the ambient air circulating within the environmental cooling chamber 308. Controller 302 may receive information from temperature sensor 308 and selectively operate primary refrigeration unit 304 and auxiliary cooling unit 306 based on the received information.

For example, when a test is initiated, controller 302 may cause primary refrigeration unit 304 to be powered on so that testing conditions can be initially achieved. Controller 302 may operate primary refrigeration unit 304 until a target temperature is achieved or until a temperature within a target range of temperatures is achieved. When controller 302 receives temperature information from temperature sensor 308 that indicates that the target temperature has been reached, controller 302 may turn off primary refrigeration unit 304 and power up auxiliary cooling unit 306. Because the load of maintaining the temperature at the target temperature is less than the load required to obtain the target temperature, the smaller, auxiliary cool unit 306 may be more efficiently operated for the maintenance of the temperature of cooling chamber 310.

Controller 302 may continue operation of cooling system 300 using auxiliary cooling unit 306 as the sole source of refrigeration until conditions require more cooling than auxiliary cooling unit 306 can provide. For example, controller 302 may continue to monitor temperature information received from temperature sensor 308. If controller 302 receives temperature information indicating that the temperature within cooling chamber 310 has increased above a desired range of acceptable temperatures, controller 302 may switch operation of cooling system 300 from auxiliary cooling unit 306 to primary refrigeration unit 304. Primary refrigeration unit 304 may then be operated until the temperature of cooling chamber 310 drops below the target temperature or to a temperature within the range of acceptable temperatures. In this manner, controller 302 may more efficiently operate cooling system 300.

In other embodiments, the operation of primary refrigeration unit 304 and auxiliary cooling unit 306 may be load based. For example, controller 302 may power on primary refrigeration unit 304 for the initial set up of the testing conditions. Controller 302 may then monitor the load on primary refrigeration unit 304. When the load on the primary refrigeration unit 304 drops below a predefined level, controller 302 may turn off primary refrigeration unit 304 and begin operation of auxiliary cooling unit 306.

For example, controller 302 may determine that the load upon primary refrigeration unit 304 to bring the cooling chamber 310 to the desired testing conditions is approximately 100 percent. However, as the temperature in cooling chamber 310 decreases and gets closer to the target temperature, the load upon primary refrigeration unit 304 decreases. When controller 302 determines that load on primary refrigeration unit 304 is below a predefined level, controller 302 may power off primary refrigeration unit 304 and power on auxiliary cooling unit 306. For example, where controller 302 determines that primary refrigeration unit is only cycling on 15 percent of the time to maintain the desired target temperature, controller 302 may switch operation of the cooling system from primary refrigeration unit 304 to auxiliary cooling unit 306.

Controller 302 may then monitor the load on auxiliary cooling unit 306. When controller 302 detects that the loading of auxiliary cooing unit 306 goes above a predefined threshold level, controller 302 may turn off auxiliary cooling unit 306 and commence operation of primary refrigeration unit 304. For example, in one particular embodiment, controller 302 may switch cooling of the system from auxiliary cooling unit 306 to primary refrigeration unit 304 when controller 302 determines that the load upon auxiliary cooling unit 306 is approximately 100 percent. Stated differently, controller 302 may switch cooling of the system to primary refrigeration unit 304 when auxiliary cooling unit 306 is cycling on 100 percent of the time.

As described above, auxiliary cooling unit 306 may include a dual stage system having dual compressors and dual heat exchangers arranged in a cascade configuration. In certain embodiments, controller 302 may control auxiliary cooling unit 306 to operate in a single stage mode. The single stage mode of auxiliary cooling unit 306 generally refers to operation of a primary compressor while the secondary compressor is powered off. Controller 302 monitor the operation of auxiliary cooling unit 306 and may switch from dual stage mode to single stage mode under certain conditions.

For example, if controller 302 determines that the load on auxiliary cooling unit 306 is low, controller 302 may power off the secondary compressor. As another example, controller 302 may receive temperature information indicating that the target temperature is above the temperature of the cooling water used to cool the heat exchangers of auxiliary cooling unit 306. Controller 302 may then power off the secondary compressor (for example, secondary compressor 154 of FIG. 1) and operate auxiliary cooling unit 306 in the single stage mode.

While operating in single stage mode, only the primary compressor of the dual stage cascade configuration is operated. Thus, returning to FIG. 1, only primary compressor 144 is operated in single stage mode. Secondary compressor 154 remains powered off, and first refrigerant 142 is cooled by heat exchanger 146. In certain embodiments, this single stage mode of operation may be appropriate where the cooling chamber 116 is maintained at a steady target temperature between 25° Celsius and 50° Celsius. However, it may be recognized that operating auxiliary cooling unit 112 in cascade mode may provide adequate cooling for temperatures ranging from 120° to −65° Celsius.

Figure 4:
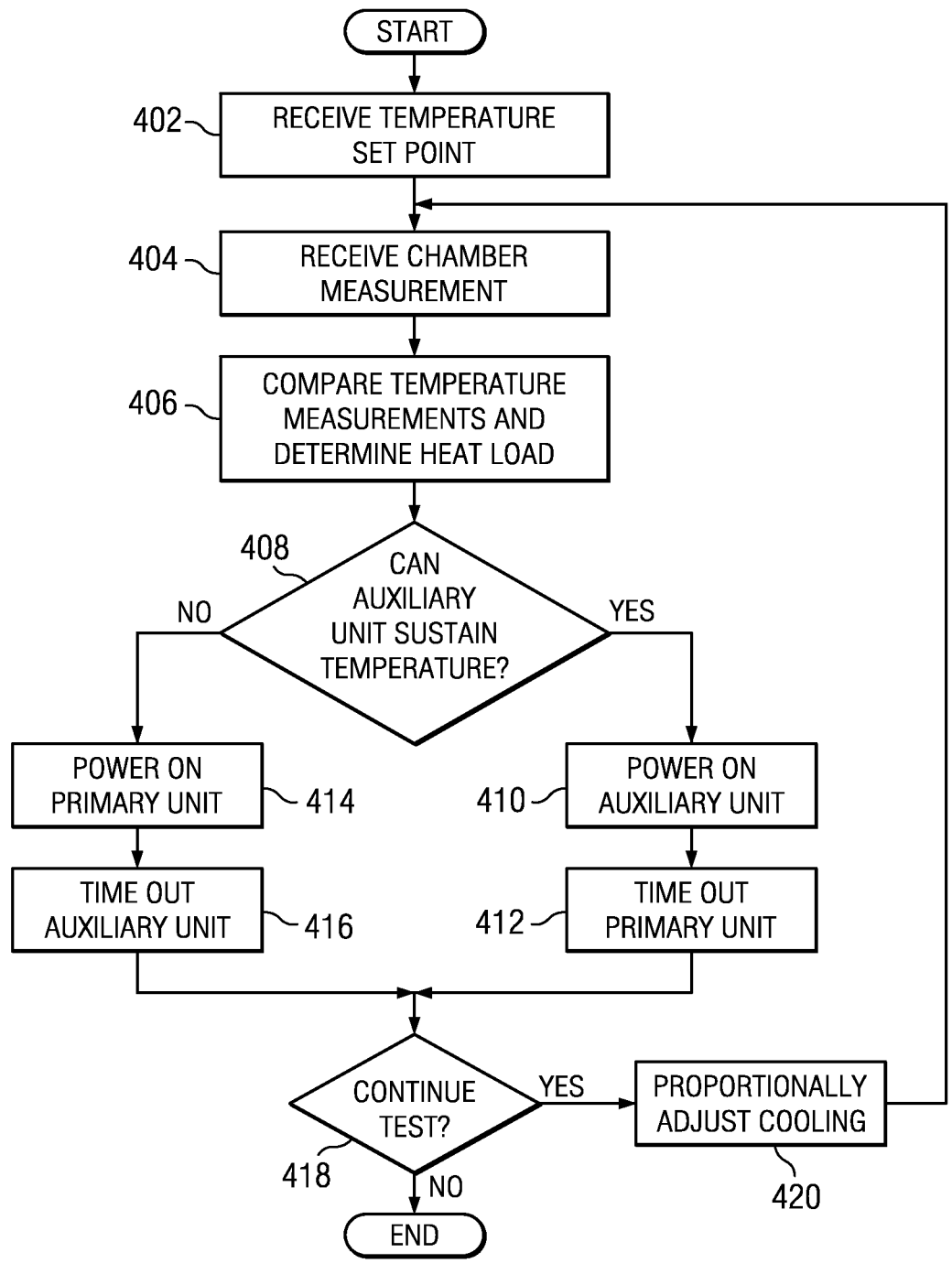
FIG. 4 illustrates an exemplary method for providing efficient cooling, according to certain embodiments of the present disclosure.

FIG. 4 illustrates an exemplary method for providing efficient cooling, according to certain embodiments of the present disclosure. The method may begins at step 402 when a temperature set-point is received. A chamber temperature measurement may then be received at step 404. The chamber temperature measurement may include a temperature reading of the inner cavity of environmental test chamber 116.

In a particular embodiment, the information received during steps 402 and 404 may be received while one of the primary refrigeration unit 114 or auxiliary cooling unit 112 are being used to cool environmental test chamber 116. Alternatively, the information may be received while both the primary refrigeration unit 114 and the auxiliary cooling unit 112 are being used to cool environmental test chamber 116.

At step 406, the temperature measurements are compared and the heat load is determined. Based on the comparisons and the heat load, a determination may be made at step 408 as to whether the auxiliary unit can sustain the target temperature. For example, where the chamber temperature measurement identifies the temperature of environmental test chamber 116 of being less than −20 degrees Celsius, it may be determined that auxiliary cooling unit 112 may be able sustain the target temperature. Likewise, where the heat load identifies that primary refrigeration unit 114 is only operating at less than 15% capacity, it may be determined that auxiliary cooling unit 112 may be able sustain the target temperature. Because auxiliary cooling unit 112 may have an energy usage level that is less than an energy usage level of primary refrigeration unit 114, the temperature of environmental test chamber 116 may be more efficiently maintained by auxiliary cooling unit 112 than the primary refrigeration unit 114. Accordingly, if it is determined that auxiliary cooling unit 112 can sustain the target temperature, the method proceeds to steps 410 and 412 where auxiliary cooling unit 112 is powered on and primary refrigeration unit 114 is timed out, respectively.

In the alternative, it may be determined at step 408 that auxiliary cooling unit 112 cannot sustain the target temperature. For example, where the chamber temperature measurement identifies the temperature of environmental test chamber 116 of being much greater than the temperature set point, it may be determined that auxiliary cooling unit 112 is not yet able sustain the target temperature. Additionally or alternatively, where the heat load identifies that primary refrigeration unit 114 is operating at greater than 50% capacity, it may be determined that auxiliary cooling unit 112 is not yet able sustain the target temperature. In such a scenario, the method proceeds to steps 414 and 416 where primary refrigeration unit 114 is powered on and auxiliary cooling unit 112 is timed out, respectively.

In either scenario, the method then continues to step 418, where it is determined if test conditions should be maintained. If the test conditions should not be further maintained, the method ends. Alternatively, if the test conditions should be maintained, the method returns to step 404 and another chamber measurement is received. The method may continue in this manner until the testing process is completed.

Although the present disclosure has been described with several embodiments, a myriad of changes, variations, alterations, transformations, and modifications may be suggested to one skilled in the art, and it is intended that the present disclosure encompass such changes, variations, alterations, transformation, and modifications as they fall within the scope of the appended claims.

What is claimed is:

1. A cooling system comprising:
    an environmental test chamber having an inner cavity;
    a primary refrigeration unit configured to cool the inner cavity of the environmental test chamber;
    an auxiliary cooling unit configured to independently cool the inner cavity of the environmental test chamber, the auxiliary cooling unit having a cooling capacity that is less than a cooling capacity of the primary refrigeration unit, the auxiliary cooling unit comprising:
        a housing that is external to the primary refrigeration unit;
        a first closed loop configured to circulate a first refrigerant between a primary compressor, a heat exchanger, a cascade exchanger, and the environmental test chamber; and
        a second closed loop configured to circulate a second refrigerant between a secondary compressor, a condensor, the cascade exchanger, and a sub-cooler, wherein the cascade exchanger is common to both the first closed loop and the second closed loop and is configured to exchange heat between the first refrigerant and the second refrigerant; and
    a controller comprising logic that is configured to:
        determine if the auxiliary cooling unit is able to sustain a target temperature; and
        in response to determining that the auxiliary cooling unit is able to sustain the target temperature, power on the auxiliary cooling unit and time out or turn off the primary refrigeration unit.

2. The cooling system of claim 1, wherein the primary compressor, secondary compressor, heat exchanger, and cascade exchanger of the auxiliary cooling unit are arranged in a cascade configuration.

3. The cooling system of claim 1, wherein the controller further comprises logic that is configured to determine that the target temperature is greater than a temperature of water being supplied to at least one of the heat exchanger or the cascade exchanger and power off at least one of the primary compressor or the secondary compressor.

4. The cooling system of claim 1, wherein the controller further comprises logic that is configured to:
    receive a chamber temperature measurement associated with the environmental test chamber;
    based on the chamber temperature measurement, determine that the auxiliary cooling unit cannot sustain the target temperature; and
    in response to determining that the auxiliary cooling unit cannot sustain the target temperature, power on the primary refrigeration unit.

5. The cooling system of claim 1, wherein the auxiliary cooling unit further comprises:
    a solenoid valve configured to selectively control removal of a portion of the first refrigerant that is transported to the environmental test chamber.

6. The cooling system of claim 1, wherein the primary refrigeration unit comprises:
    a third closed loop configured to circulate a third refrigerant between a second primary compressor, a primary heat exchanger, and the environmental test chamber; and
    a fourth closed loop configured to circulate a fourth refrigerant between a second secondary compressor and at least one secondary heat exchanger.

7. The cooling system of claim 1, wherein the controller is configured to determine that the auxiliary cooling unit is able to sustain the target temperature in response to determining that the primary refrigeration unit is operating less than 15 percent of a given time.

8. A cooling system comprising:
   an auxiliary cooling unit configured to provide auxiliary cooling of an environmental test chamber independently of a primary refrigeration unit, the auxiliary cooling unit having a cooling capacity less than a cooling capacity of the primary refrigeration unit, the auxiliary cooling unit comprising:
   a housing that is external to the primary refrigeration unit;
   a first closed loop configured to circulate a first refrigerant between a primary compressor, a heat exchanger, a cascade exchanger, and the environmental test chamber; and
   a second closed loop configured to circulate a second refrigerant between a secondary compressor, a condensor, the cascade exchanger, and a sub-cooler, wherein the cascade exchanger is common to both the first closed loop and the second closed loop and is configured to exchange heat between the first refrigerant and the second refrigerant; and
   a controller comprising logic that is configured to:
   determine if the auxiliary cooling unit is able to sustain a target temperature; and
   in response to determining that the auxiliary cooling unit is able to sustain the target temperature, transmit a signal to power on the auxiliary cooling unit and transmit a signal to time out or turn off the primary refrigeration unit.

9. The cooling system of claim 8, wherein the primary compressor, secondary compressor, heat exchanger, and cascade exchanger of the auxiliary cooling unit are arranged in a cascade configuration.

10. The cooling system of claim 8, wherein the controller further comprises logic that is configured to determine that the target temperature is greater than a temperature of water being supplied to at least one of the heat exchanger or the cascade exchanger and power off at least one of the primary compressor or the secondary compressor.

11. The cooling system of claim 8, wherein the controller further comprises logic that is configured to:
   receive a chamber temperature measurement associated with the environmental test chamber;
   based on the chamber temperature measurement, determine that the auxiliary cooling unit cannot sustain the target temperature; and
   in response to determining that the auxiliary cooling unit cannot sustain the target temperature, transmit a signal to power on the primary refrigeration unit.

12. The cooling system of claim 8, wherein the auxiliary cooling unit further comprises:
   a solenoid valve configured to selectively control removal of a portion of the first refrigerant that is transported to the environmental test chamber.

13. The cooling system of claim 8, wherein the controller is configured to determine that the auxiliary cooling unit is able to sustain the target temperature in response to determining that the primary refrigeration unit is operating less than 15 percent of a given time.

14. A method for cooling, comprising:
   communicating, at a controller, with an auxiliary cooling unit and a primary refrigeration unit, the auxiliary cooling unit configured to independently provide auxiliary cooling of an environmental test chamber, the auxiliary cooling unit having a cooling capacity less than a cooling capacity of the primary refrigeration unit, the auxiliary cooling unit comprising:
   a housing that is external to the primary refrigeration unit;
   a first closed loop configured to circulate a first refrigerant between a primary compressor, a heat exchanger, a cascade exchanger, and the environmental test chamber; and
   a second closed loop configured to circulate a second refrigerant between a secondary compressor, a condensor, the cascade exchanger, and a sub-cooler, wherein the cascade exchanger is common to both the first closed loop and the second closed loop and is configured to exchange heat between the first refrigerant and the second refrigerant;
   receiving information associated with a first chamber temperature measurement, the first chamber temperature measurement associated with the environmental test chamber;
   based on the first chamber temperature measurement, determining using logic of the controller that the auxiliary cooling unit is able to sustain a target temperature; and
   in response to determining that the auxiliary cooling unit is able to sustain the target temperature, transmitting a signal to power on the auxiliary cooling unit and transmitting a signal to time out or turn off the primary refrigeration unit using the controller.

15. The method of claim 14, wherein the primary compressor, secondary compressor, heat exchanger, and cascade exchanger of the auxiliary cooling unit are arranged in a cascade configuration.

16. The method of claim 14, further comprising:
   determining that the target temperature is greater than a temperature of water being supplied to at least one of the heat exchanger or the cascade exchanger; and
   powering off at least one of the primary compressor or the secondary compressor.

17. The method of claim 14, further comprising:
   receiving a second chamber temperature measurement associated with the environmental test chamber;
   based on the second chamber temperature measurement, determining that the auxiliary cooling unit cannot sustain the target temperature; and
   in response to determining that the auxiliary cooling unit cannot sustain the target temperature, transmitting a signal to power on the primary refrigeration unit.

18. The method of claim 14, further comprising:
   operating a solenoid valve to selectively control removal of a portion of the first refrigerant that is transported to the environmental test chamber.

19. The method of claim 14, wherein determining that the auxiliary cooling unit is able to sustain the target temperature comprises determining that the primary refrigeration unit is operating less than 15 percent of a given time.

20. The method of claim 14, further comprising:
   circulating a third refrigerant in a third closed loop that couples a second primary compressor, a primary heat exchanger, and the environmental test chamber; and
   circulating a fourth refrigerant in a fourth closed loop that couples a second secondary compressor and at least one secondary heat exchanger.

* * * * *